United States Patent
Nakamura et al.

(10) Patent No.: US 8,455,677 B2
(45) Date of Patent: Jun. 4, 2013

(54) METHANOL DEHYDROGENATION CATALYST FOR PRODUCING OF METHYL FORMATE AND METHOD FOR PRODUCING METHYL FORMATE

(75) Inventors: Kenji Nakamura, Niigata (JP); Hideaki Ogino, Niigata (JP); Yoriko Obata, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/121,245

(22) PCT Filed: Sep. 14, 2009

(86) PCT No.: PCT/JP2009/066024
§ 371 (c)(1),
(2), (4) Date: Jun. 20, 2011

(87) PCT Pub. No.: WO2010/035653
PCT Pub. Date: Apr. 1, 2010

(65) Prior Publication Data
US 2011/0245532 A1    Oct. 6, 2011

(30) Foreign Application Priority Data
Sep. 26, 2008   (JP) ................................ 2008-247614

(51) Int. Cl.
*C07C 67/40*    (2006.01)
(52) U.S. Cl.
USPC .......................................... 560/239; 502/208

(58) Field of Classification Search
None
See application file for complete search history.

(56) References Cited

U.S. PATENT DOCUMENTS 4,436,835 A    3/1984    Horie et al.

FOREIGN PATENT DOCUMENTS

| JP | 53-71008 | 6/1978 |
| JP | 54-12315 | 1/1979 |
| JP | 58-163444 | 9/1983 |
| JP | 3-151047 | 6/1991 |
| JP | 10-245359 | 9/1998 |
| JP | 10-306053 | 11/1998 |

OTHER PUBLICATIONS

White et al, Basic Energy Sciences Advisory Committee Subpanel Workshop Report, Opportunities for Catalysis in the 21st Century, 2002, pp. 1-47.*
PHOTIS, "Halide-directed . . . ", Tetrahedron Letters, 1980, pp. 3539-3540.

* cited by examiner

*Primary Examiner* — Paul A Zucker
(74) *Attorney, Agent, or Firm* — Greenblum & Bernstein, P.L.C.

(57) ABSTRACT

A methanol dehydrogenating catalyst used for production of methyl formate, which contains a copper-zinc-aluminum oxide, a phosphoric acid compound, and an alkali metal bromide, wherein the catalyst has high methyl formate selectivity and excellent durability and heat resistance; and a method of producing methyl formate by using the catalyst.

9 Claims, No Drawings

METHANOL DEHYDROGENATION CATALYST FOR PRODUCING OF METHYL FORMATE AND METHOD FOR PRODUCING METHYL FORMATE

TECHNICAL FIELD

The present invention relates to a catalyst used for production of methyl formate through the dehydrogenation reaction of methanol in a gas phase, and to a method of producing methyl formate by using the catalyst.

BACKGROUND ART

Methyl formate is produced as an intermediate in organic synthesis and is an industrially important raw material for high-purity carbon monoxide, formic acid, formaldehyde, acetic acid, N,N-dimethylformamide, or the like.

There are reported a large number of catalysts for synthesizing methyl formate through the dehydrogenation of methanol in a gas phase. Most of the catalysts are formed of copper as the main component. For example, Patent Document 1 discloses a catalyst consisting of copper, zinc, zirconium, and aluminum, and Patent Document 2 discloses a catalyst consisting of copper oxide, zinc oxide, and aluminum oxide.

There are also proposed catalysts each containing a co-catalyst. For example, Patent Document 3 discloses a method of producing a catalyst by adding a phosphate of copper or the like, a chloride of an alkali metal, alkali earth metal, or the like, and an alkali metal or alkali earth metal compound excluding halides to a mixture of copper oxide, zinc oxide, and aluminum oxide. Patent Document 4 discloses a catalyst consisting of a copper-zinc-aluminum oxide, a phosphoric acid compound, and two or more kinds of alkali metal compounds including lithium.

In the catalyst described in Patent Document 1 or 2 among those catalysts, the content of copper must be increased to improve the methyl formate yield and selectivity. Therefore, the mechanical strength of the catalyst after reductive activation is greatly reduced.

According to the method described in Patent Document 3, it is said that a catalyst having high mechanical strength even after reductive activation and having high methyl formate yield and selectivity can be produced by the function of an additive. With the catalyst described in Patent Document 4, an initial activity and the methyl formate selectivity are further improved, and it is assumed that this is mainly due to an effect obtained by adding lithium.

However, further improvement is required for the practical use of those catalysts from the viewpoint of methyl formate selectivity, durability and heat resistance.

PRIOR ART DOCUMENTS

Patent Documents
[Patent Document 1] JP-A-53-71008
[Patent Document 2] JP-A-54-12315
[Patent Document 3] JP-A-58-163444
[Patent Document 4] JP-A-3-151047

SUMMARY OF INVENTION

Technical Problem

It is an object of the present invention to provide a methanol dehydrogenating catalyst used for production of methyl formate, which has high methyl formate selectivity and excellent durability and heat resistance, and a method of producing methyl formate by using the catalyst.

Solution to Problem

The inventors of the present invention have conducted intensive studies on a catalyst which is formed of a copper-zinc-aluminum oxide, a phosphoric acid compound, and an alkali metal compound in order to solve the above-mentioned problem. As a result, the inventors have found that a catalyst containing an alkali metal bromide as the alkali metal compound has apparently higher methyl formate selectivity than a conventional catalyst containing an alkali metal chloride as the alkali metal compound, and has excellent durability and heat resistance, that is, small time-dependent reductions in durability and heat resistance in a durability test and a heat resistance test. Thus, the present invention has been accomplished.

That is, the present invention provides as follows:

A methanol dehydrogenating catalyst used for production of methyl formate, which contains a copper-zinc-aluminum oxide, a phosphoric acid compound, and an alkali metal bromide; and a method of producing methyl formate, including dehydrogenating methanol in a gas phase by using the catalyst.

Advantageous Effects of Invention

The catalyst of the present invention has excellent durability and heat resistance and high methyl formate selectivity. By dehydrogenating methanol in a gas phase with the catalyst of the present invention, methyl formate can be produced high-selectively at a high yield.

DESCRIPTION OF EMBODIMENTS

The catalyst of the present invention exhibits an activity, in particular, high methyl formate selectivity and heat resistance in the production of methyl formate by the dehydrogenation of methanol in a gas phase. The reason that such an effect is obtained seems to be that an alkali metal bromide is contained as the alkali metal compound. The reason that a catalyst containing an alkali metal bromide as the alkali metal compound is superior in methyl formate selectivity and heat resistance to a catalyst containing an alkali metal chloride is not known. However, the following reasons are conceivable.

(1) The catalyst containing an alkali metal bromide has a lower degree of sublimation of the halogen during a reaction than the catalyst containing an alkali metal chloride. Therefore, the development of methyl formate decomposition reactivity by an alkali metal as a side reaction is suppressed by electron release from the halogen to the alkali metal, resulting in high selectivity.

(2) The catalyst containing an alkali metal bromide hardly changes in composition even during the reaction. Therefore, collapse on the surface of the catalyst hardly occurs, so heat resistance is improved.

The method of producing a copper-zinc-aluminum oxide as the skeleton of a catalyst component in the catalyst of the present invention is not particularly limited if copper, zinc, and aluminum catalytic components are uniformly mixed together. To obtain a homogeneous mixture of copper, zinc, and aluminum catalytic components, for example, a method in which an aqueous solution of a water-soluble salt of each catalytic component and an alkaline aqueous solution are mixed together to prepare precipitates and the precipitates are then mixed together, a method in which water-soluble salts of two catalytic catalysts out of copper, zinc, and aluminum are coprecipitated and a precipitate of the other catalytic component is mixed with the coprecipitate, and a method in which a coprecipitate of water-soluble salts of three catalytic components, copper, zinc, and aluminum is obtained may be employed, for example. Note that the precipitate or coprecipitate of each catalytic component does not need to be an oxide in the stage of precipitate or coprecipitate if it can be converted into an oxide in the subsequent drying or baking step (oxide precursor).

As a raw material which may become an oxide of copper, there can be used, for example, water-soluble organic salts such as copper acetate or water-soluble inorganic salts such as copper chloride, copper sulfate, and copper nitrate.

As a raw material which may become an oxide of zinc, there can be used, for example, zinc oxide and water-soluble organic salts such as zinc acetate or water-soluble inorganic salts such as zinc chloride, zinc sulfate, and zinc nitrate.

As a raw material which may become an oxide of aluminum, there can be used, for example, in addition to aluminum oxide and alumina sol, water-soluble organic salts such as aluminum acetate or water-soluble inorganic salts such as aluminum chloride, aluminum sulfate, and aluminum nitrate.

As the precipitant used for obtaining a precipitate or a coprecipitate, there are used, for example, alkali hydroxide, alkali carbonate, and alkali bicarbonate, and specific examples thereof include sodium hydroxide, sodium carbonate, potassium carbonate, sodium bicarbonate, and ammonium bicarbonate.

The methanol dehydrogenating catalyst used for production of methyl formate of the present invention can be produced by adding a phosphoric acid compound and an alkali metal bromide to the above-mentioned copper-zinc-aluminum oxide or oxide precursor and drying and baking the obtained mixture.

The method of adding a phosphoric acid compound and an alkali metal bromide is not particularly limited if they are uniformly mixed together and may be a wet or dry process. The drying temperature is preferably about 70 to 150° C., and the baking temperature is preferably about 350 to 650° C.

The catalyst of the present invention is pelletized before use. Reduction is preferably carried out before the reaction.

As the phosphoric acid compound, a phosphate, monohydrogenphosphate, dihydrogenphosphate, pyrophosphate, or the like of copper, zinc, or aluminum is preferably used, and specific examples thereof include cupric phosphate, copper pyrophosphate, zinc phosphate, aluminum phosphate, aluminum monohydrogenphosphate, and aluminum dihydrogenphosphate.

Examples of the alkali metal bromide include lithium bromide, sodium bromide, and potassium bromide. From the viewpoints of methyl formate selectivity, heat resistance, and durability, preferred is lithium bromide or sodium bromide, and particularly preferred is sodium bromide.

It is preferred from the viewpoint of the reactivity of the catalyst that the appropriate sintering of a copper atom should occur. "Sintering" means a phenomenon that the catalyst particles agglomerate into a coarse grain. When the catalyst particles agglomerate into a coarse grain, the area of the contact reaction interface between the catalyst particles and methanol decreases, and the number of sites serving as catalyst active points falls, whereby the conversion of methanol may drop. Meanwhile, appropriate sintering slightly reduces the surface area of the catalyst, thereby making it possible to stabilize the catalyst in terms of oxidation resistance and the like.

From those viewpoints, as for the content ratio of each component in the catalyst of the present invention, when the total number of copper atoms contained in the catalyst is 10, the atomic ratio of zinc is preferably 0.1 to 10, more preferably 0.15 to 5, and further preferably 0.2 to 2, and the atomic ratio of aluminum is preferably 0.1 to 10, more preferably 0.15 to 5, and further preferably 0.2 to 2. Further, as for the content ratio of the phosphoric acid compound in the catalyst of the present invention, when the total number of copper atoms contained in the catalyst is 10, the atomic ratio of phosphorus is preferably 0.1 to 5, more preferably 0.15 to 5, and further preferably 0.2 to 2. As for the content ratio of the alkali metal bromide, when the total number of copper atoms contained in the catalyst is 10, the atomic ratio of bromine is preferably 0.02 to 0.5, more preferably 0.03 to 0.4, and particularly preferably 0.05 to 0.3.

Note that the content ratio of each component in the copper-zinc-aluminum oxide is appropriately determined to ensure that the content ratio of each component in the catalyst of the present invention falls within the above-mentioned range in consideration of the number of copper, zinc, or aluminum atoms contained in the phosphoric acid compound.

Methyl formate can be produced high-selectively at a high yield by dehydrogenating methanol in a gas phase with the catalyst of the present invention. The reaction conditions are appropriately determined from the viewpoints of the yield, production cost, and the like of methyl formate. The reaction temperature is preferably 100 to 400° C., more preferably 150 to 350° C. The space velocity (gas hour space velocity: GHSV) of methanol is preferably 100 to 100,000/hr, more preferably 500 to 30,000/hr. The reaction pressure is preferably 5 MPa-G or less, more preferably 1 MPa-G or less, and is preferably 0.01 MPa-G or more, more preferably 0.1 MPa-G or more, in terms of gauge pressure.

EXAMPLES

The following examples and comparative examples are provided for the purpose of further illustrating the present invention but are in no way to be taken as limiting.

<Preparation of Catalyst>

Example 1

186.6 g (0.772 mol) of copper nitrate trihydrate, 11.5 g (0.039 mol) of zinc nitrate hexahydrate, and 28.9 g (0.077 mol) of aluminum nitrate nonahydrate were dissolved in 1,600 g of ion exchange water and heated to 40° C. The resulting solution was injected into an aqueous solution at 40° C. prepared by dissolving 108.0 g (1.019 mol) of anhydrous sodium carbonate in 1,600 g of ion exchange water over 1 minute under agitation. The resulting solution was aged by heating at 40° C. for 60 minutes and further at 80° C. for 30 minutes, and a precipitate was separated by filtration and washed with water to obtain 282 g of a coprecipitate.

20.3 g (0.020 mol as $Al_2O_3$) of 10 mass % alumina sol, 4.9 g (0.013 mol) of cupric phosphate, 2.5 g (0.006 mol) of trisodium phosphate dodecahydrate, and 0.8 g (0.008 mol) of sodium bromide were added to and kneaded with the coprecipitate, and the kneaded product was dried at 115° C. for 12 hours and further baked at 600° C. for 2 hours. The obtained oxide was ground, 3 mass % of graphite were added to the ground product, and the resulting mixture was tableted by a tableting machine to obtain a columnar tablet catalyst having a diameter of 6 mm and a height of 5.5 mm. As a result of elemental analysis, the number of bromine atom was 0.10 (atomic ratio), when the total number of copper atoms contained in the obtained catalyst was 10. ICP emission spectral analysis was used for the elemental analysis.

Example 2

A catalyst was prepared in accordance with the preparation method described in Example 1 except that 1.6 g (0.016 mol)

of sodium bromide were added in place of 0.8 g of sodium bromide. As a result of elemental analysis, the number of bromine atom was 0.20 (atomic ratio), when the total number of copper atoms contained in the obtained catalyst was 10.

Example 3

A catalyst was prepared in accordance with the preparation method described in Example 1 except that 2.5 g (0.024 mol) of sodium bromide were added in place of 0.8 g of sodium bromide. As a result of elemental analysis, the number of bromine atom was 0.30 (atomic ratio), when the total number of copper atoms contained in the obtained catalyst was 10.

Example 4

A catalyst was prepared in accordance with the preparation method described in Example 1 except that 0.7 g (0.008 mol) of lithium bromide was added in place of 0.8 g of sodium bromide. As a result of elemental analysis, the number of bromine atom was 0.10 (atomic ratio), when the total number of copper atoms contained in the obtained catalyst was 10.

Example 5

A catalyst was prepared in accordance with the preparation method described in Example 1 except that 1.0 g (0.008 mol) of potassium bromide was added in place of 0.8 g of sodium bromide. As a result of elemental analysis, the number of bromine atom was 0.10 (atomic ratio), when the total number of copper atoms contained in the obtained catalyst was 10.

Comparative Example 1

A catalyst was prepared in accordance with the preparation method described in Example 1 except that sodium bromide was not added.

Comparative Example 2

A catalyst was prepared in accordance with the preparation method described in Example 1 except that 0.34 g (0.008 mol) of lithium chloride was added in place of 0.8 g of sodium bromide. As a result of elemental analysis, the number of chlorine atom was 0.10 (atomic ratio), when the total number of copper atoms contained in the obtained catalyst was 10.

Comparative Example 3

A catalyst was prepared in accordance with the preparation method described in Example 1 except that 0.2 g (0.008 mol) of lithium fluoride was added in place of 0.8 g of sodium bromide. As a result of elemental analysis, the number of fluorine atom was 0.10 (atomic ratio), when the total number of copper atoms contained in the obtained catalyst was 10.

Comparative Example 4

A catalyst was prepared in accordance with the preparation method described in Example 1 except that 1.1 g (0.008 mol) of lithium iodide were added in place of 0.8 g of sodium bromide. As a result of elemental analysis, the number of iodine atom was 0.10 (atomic ratio), when the total number of copper atoms contained in the obtained catalyst was 10.

Comparative Example 5

A catalyst was prepared in accordance with the preparation method described in Example 1 except that 0.5 g (0.008 mol) of sodium chloride was added in place of 0.8 g of sodium bromide. As a result of elemental analysis, the number of chlorine atom was 0.10 (atomic ratio), when the total number of copper atoms contained in the obtained catalyst was 10.

<Primary Evaluation Test of Catalyst (Screening)>

To evaluate the activity and heat resistance of a catalyst, methanol conversion and methyl formate selectivity were measured at higher temperature and higher space velocity (GHSV) conditions than the ordinary reaction conditions. Specifically, the obtained molded tablet was first ground, and ground pieces having a size of 20 to 30 mesh were sieved out. The ground product was reduced at 220° C. in a hydrogen stream, and 0.5 ml of the product was weighed and filled into a reaction tube having an inner diameter of 6 mm. A reaction was carried out at a reaction control temperature of 360° C., a reaction pressure of 0.49 MPa-G, and a methanol GHSV of 100,000/hr for 20 hours to measure methanol conversion and methyl formate selectivity.

The methanol (MeOH) conversion and methyl formate (MF) selectivity were determined from the composition of a gas at the outlet of the reactor based on the following equation. [CO], [CH4], [CO2], [DME], [MeOH], and [MF] in the equation denote the concentrations (mol %) of carbon monoxide, methane, carbon dioxide, dimethyl ether, methanol, and methyl formate in the gas at the outlet of the reactor, respectively.

Methanol conversion (mol %)=([CO]+[CH4]+[CO2]+([DME]+[MF])×2)/([CO]+[CH4]+[CO2]+([DME]+[MF])×2+[MeOH])×100

Methyl formate selectivity (mol %)=([MF]×2)/([CO]+[CH4]+[CO2]+([DME]+[MF])×2)×100

The primary evaluation test results of the catalysts of Examples 1 to 5 and Comparative Examples 1 to 5 are shown in Table 1. The values are the average values for 20 hours.

TABLE 1

| Catalyst | Alkali metal halide | Atomic ratio of halogen | MeOH conversion (mol %) | MF selectivity (mol %) | MF yield (mol %) |
|---|---|---|---|---|---|
| Example 1 | NaBr | 0.10 | 42.2 | 94.4 | 39.8 |
| Example 2 | NaBr | 0.20 | 42.6 | 95.3 | 40.6 |
| Example 3 | NaBr | 0.30 | 40.6 | 96.6 | 39.2 |
| Example 4 | LiBr | 0.10 | 41.5 | 94.3 | 39.1 |
| Example 5 | KBr | 0.10 | 39.4 | 95.4 | 37.6 |
| Comparative Example 1 | none | — | 38.1 | 90.9 | 34.6 |
| Comparative Example 2 | LiCl | 0.10 | 40.1 | 93.0 | 37.3 |
| Comparative Example 3 | LiF | 0.10 | 38.2 | 93.1 | 35.6 |
| Comparative Example 4 | LiI | 0.10 | 39.0 | 91.9 | 35.8 |
| Comparative Example 5 | NaCl | 0.10 | 39.9 | 92.9 | 37.1 |

The atomic ratio of halogen is the number of halogen atom when the total number of copper atoms contained in the catalyst was 10.

As shown in Table 1, the catalysts of Examples 1 to 5, in each of which an alkali metal bromide was added, each showed a higher MeOH conversion and MF selectivity than the catalyst of Comparative Example 1 in which no alkali metal bromide was added. The catalysts of Examples 1 to 5 each showed better MF selectivity and MF yield than the catalysts of Comparative Examples 2, 3, 4, and 5 in each of which the halogen species was not bromine.

<Durability Test>

In accordance with the same method as that of the primary evaluation test, a time-dependent change in each yield was investigated at high temperature and high space velocity (GHSV) conditions by extending the reaction time to 40 hours. The durability of the catalyst was expressed as an average deterioration rate (%/hr). The average deterioration rate was determined by calculating a reduction in yield per unit time from the difference between MF yield after 5 hours of the reaction and MF yield after 40 hours of the reaction. The lower average deterioration rate means more excellent durability.

The durability test results of Examples 1, 4, and 5 and Comparative Examples 2 and 5 are shown in Table 2.

TABLE 2

| | Catalyst | | | | |
|---|---|---|---|---|---|
| | Example 1 | Example 4 | Example 5 | Comparative Example 2 | Comparative Example 5 |
| | | | Alkali metal halide | | |
| Reaction time | NaBr | LiBr | KBr | LiCl | NaCl |
| | | | MF yield | | |
| (hr) | (mol %) | (mol %) | (mol %) | (mol %) | (mol %) |
| 5 | 40.4 | 40.1 | 38.6 | 38.7 | 38.6 |
| 10 | 39.6 | 38.8 | 37.1 | 37.2 | 36.8 |
| 20 | 38.7 | 37.4 | 35.5 | 34.9 | 34.7 |
| 30 | 36.9 | 35.2 | 33.3 | 32.3 | 32.0 |
| 40 | 35.4 | 33.2 | 31.1 | 29.4 | 29.4 |
| Average deterioration rate (%/hr) | 0.14 | 0.19 | 0.21 | 0.26 | 0.26 |

As shown in Table 2, the catalysts of Examples 1, 4, and 5, in each of which an alkali metal bromide was added, each showed a lower deterioration rate represented by a time-dependent change in yield than the catalysts of Comparative Examples 2 and 5 in each of which an alkali metal chloride was added. Therefore, the catalyst of the present invention obtained by adding a bromide as the halogen species is superior in durability to the catalysts of Comparative Examples 2 and 5 in each of which a chloride was added as the halogen species.

<Test for Evaluating Service Life of Catalyst>

To compare and evaluate the heat resistance and durability of the catalysts of Example 1 and Comparative Example 2, time-dependent changes in methanol conversion and methyl formate selectivity were measured at a higher temperature condition than the ordinary reaction condition.

Specifically, the obtained molded tablet was first ground, and the ground pieces each having a size of 0.85 to 1.4 mm were sieved out. The ground product was reduced at 220° C. in a hydrogen stream, and 3 ml of the product were weighed and filled into a reaction tube having an inner diameter of 10 mm. The test was continued at a reaction control temperature of 360° C. (measured at 260 to 280° C. only at the time of measurement), a reaction pressure of 0.49 MPa-G, and a methanol GHSV of 4,000/hr until the methyl formate (MF) yield at each reaction temperature became 20%. The test results are shown in Tables 3 and 4.

TABLE 3

Test on service life of catalyst (alkali component: NaBr) of Example 1

| Reaction temperature (° C.) | Elapsed time (hr) | MeOH conversion (mol %) | MF selectivity (mol %) | MF yield (mol %) |
|---|---|---|---|---|
| 260 | 0 | 32.7 | 94.4 | 30.8 |
| | 100 | 26.6 | 96.5 | 25.7 |
| | 200 | 22.8 | 96.3 | 22.0 |
| | 310 | 20.4 | 96.1 | 19.6 |
| 270 | 0 | 34.1 | 94.9 | 32.4 |
| | 100 | 30.7 | 96.1 | 29.5 |
| | 310 | 24.3 | 95.8 | 23.3 |
| | 852 | 20.7 | 96.6 | 20.0 |
| 280 | 174 | 32.4 | 95.4 | 30.9 |
| | 500 | 26.5 | 96.0 | 25.5 |
| | 810 | 24.9 | 96.2 | 24.0 |
| | 1,005 | 23.7 | 96.3 | 22.8 |

TABLE 4

Test on service life of catalyst (alkali component: LiCl) of Comparative Example 2

| Reaction temperature (° C.) | Elapsed time (hr) | MeOH conversion (mol %) | MF selectivity (mol %) | MF yield (mol %) |
|---|---|---|---|---|
| 260 | 0 | 33.1 | 94.9 | 31.4 |
| | 100 | 30.3 | 96.6 | 29.3 |
| | 200 | 26.3 | 96.7 | 25.4 |
| | 320 | 20.9 | 96.2 | 20.1 |
| 270 | 0 | 34.9 | 95.0 | 33.1 |
| | 100 | 33.6 | 95.4 | 32.0 |
| | 303 | 25.3 | 96.1 | 24.3 |
| | 416 | 21.1 | 95.9 | 20.1 |
| 280 | 214 | 33.6 | 95.1 | 32.0 |
| | 397 | 25.5 | 95.6 | 24.4 |
| | 503 | 21.4 | 95.6 | 20.5 |

As shown in Tables 3 and 4, with the catalyst of Example 1 in which an alkali metal bromide was added, the time elapsed until the MF yield reached 20% was extended 2 times or more at a higher temperature, for example, 270° C. or 280° C. as compared with the catalyst of Comparative Example 2 in which an alkali metal chloride was added. Therefore, the catalyst of the present invention is excellent in heat resistance.

Industrial Applicability

The catalyst of the present invention is excellent in durability and heat resistance and can be used to produce methyl formate from methanol high-selectively at a high yield.

Methyl formate produced by using the catalyst of the present invention is industrially useful as a raw material for high-purity carbon monoxide, formic acid, formaldehyde, acetic acid, N,N-dimethylformamide, or the like.

The invention claimed is:

1. A methanol dehydrogenating catalyst used for production of methyl formate, which comprises a copper-zinc-aluminum oxide, a phosphoric acid compound, and an alkali metal bromide.

2. The methanol dehydrogenating catalyst used for production of methyl formate according to claim 1, wherein the ratio of copper atoms to bromine atoms in the alkali metal bromide is in a range of 10:0.02 to 10:0.5.

3. The methanol dehydrogenating catalyst used for production of methyl formate according to claim 1, wherein the alkali metal bromide is selected from the group consisting of lithium bromide, sodium bromide, and potassium bromide.

4. The methanol dehydrogenating catalyst used for production of methyl formate according to claim 1, wherein the alkali metal bromide is lithium bromide or sodium bromide.

5. The methanol dehydrogenating catalyst used for production of methyl formate according to claim 1, wherein the ratio of copper atoms to zinc atoms is in a range of 10:0.1 to 10:10.

6. The methanol dehydrogenating catalyst used for production of methyl formate according to claim 1, wherein the ratio of the copper atoms to aluminum atoms is in a range of 10:0.1 to 10:10.

7. The methanol dehydrogenating catalyst used for production of methyl formate according to claim 1, wherein the ratio of copper atoms to phosphorus atoms in the phosphoric acid compound is in a range of 10:0.1 to 10:0.5.

8. A method of producing methyl formate, comprising dehydrogenating methanol in a gas phase by using the methanol dehydrogenating catalyst used for production of methyl formate according to claim 1.

9. The methanol dehydrogenating catalyst according to claim 1, wherein the phosphoric acid compound is a phosphate, monohydrogenphosphate, dihydrogenphosphate, or pyrophosphate of copper, zinc, or aluminum.

\* \* \* \* \*